United States Patent [19]
Augustine

[11] Patent Number: 5,733,320
[45] Date of Patent: Mar. 31, 1998

[54] SOURCE OF INFLATING MEDIUM WITH ACTIVE NOISE CANCELLATION FOR AN INFLATABLE THERMAL CARE APPARATUS

[75] Inventor: Scott Douglas Augustine, Bloomington, Minn.

[73] Assignee: Augustine Medical, Inc., Eden Prairie, Minn.

[21] Appl. No.: 383,880

[22] Filed: Feb. 6, 1995

[51] Int. Cl.[6] ........................................ A61F 7/00
[52] U.S. Cl. ........................ 607/107; 15/483; 454/906
[58] Field of Search .................... 454/906; 62/3.7, 62/296; 607/104, 107; 5/481, 482

[56] References Cited

U.S. PATENT DOCUMENTS

| | | | |
|---|---|---|---|
| 4,572,188 | 2/1986 | Augustine et al. | 128/380 |
| 5,106,373 | 4/1992 | Augustine et al. | 604/113 |
| 5,165,400 | 11/1992 | Berke | 128/400 |
| 5,300,098 | 4/1994 | Philipot | 607/107 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,350,417 | 9/1994 | Augustine | 607/104 |
| 5,545,196 | 8/1996 | Falk | 607/107 |

FOREIGN PATENT DOCUMENTS

| | | | |
|---|---|---|---|
| 2830606 | 1/1980 | Germany | 454/906 |
| 0 113 420 | 11/1983 | Germany . | |
| 4324051 | 11/1992 | Japan | 454/906 |
| 5223333 | 8/1993 | Japan | 454/906 |
| 5223334 | 8/1993 | Japan | 454/906 |
| 6201182 | 7/1994 | Japan | 454/906 |

OTHER PUBLICATIONS

DIGISONIX, "Digital Sound Cancellation Systems for Active Noise Control", 4 pp., D-DS-1/191, 1990.

*Primary Examiner*—Robert L. Nasser
*Attorney, Agent, or Firm*—Baker, Maxham, Jester & Meador

[57] ABSTRACT

An electrically operated source provides a stream of thermally-controlled inflating medium to inflate an inflatable thermal care apparatus for treating a hospital patient while employing active noise cancellation to reduce noise created by the source, thereby provides a reduced noise treatment device for treating hypothermic patients.

15 Claims, 2 Drawing Sheets

5,733,320

SOURCE OF INFLATING MEDIUM WITH ACTIVE NOISE CANCELLATION FOR AN INFLATABLE THERMAL CARE APPARATUS

BACKGROUND OF THE INVENTION

1. Field of the Invention

The present invention relates to a system for maintaining or changing the body temperature of a hospital patient during periods of convalescence or surgery. More specifically, the invention concerns an electrically operated source of thermally-controlled fluid, employing active noise cancellation to reduce motor noise. In an illustrative embodiment, the fluid source may be operated to provide heated fluid to inflate a warming apparatus used to treat hypothermic hospital patients.

2. Description of the Related Art

In many cases, the body temperature of a hospital patient must be regulated by lowering or elevating it to a specific level. This is often the case before, during, or after certain forms of medical treatment, such as surgery. Hospital patients, for example, sometimes become susceptible to hypothermia due to certain types of ailments or medical procedures. Therefore, medical personnel frequently must heat patients to increase their body temperature, and prevent hypothermia from setting in.

For this purpose, a number of different devices are available. Some simple examples include wool, cotton, or electric blankets. In other cases, doctors and nurses might use a warm bath. However, one of the most convenient and effective systems for treating hypothermia has been the inflatable convective thermal care apparatus, many variations of which have been developed by Augustine Medical, Inc.

One example of an inflatable convective thermal care apparatus is shown in U.S. Pat. No. 4,572,188, which issued on Feb. 25, 1986 in the name of Augustine et al. The '188 device provides an airflow cover comprising a plurality of inflatable chambers joined to form an inflatable array that covers the patient's body. After a thermally-controlled inflating medium is introduced through an entry port in the cover, it circulates through and inflates the tubes, and finally exits toward the patient through exit apertures formed in the cover, thereby bathing the patient in the fluid. This apparatus may also be referred to as an "Augustine-type thermal blanket".

Another variation of the inflatable convective thermal care apparatus employs a flexible body that is inflated with a thermally-controlled fluid to generally form a "U" shape. Fluid is received by the body into an internal chamber, from where it is expelled through a plurality of holes in the body. This causes the patient, who is surrounded by the U-shaped body, to be bathed with the thermally-controlled inflating medium. Examples of this apparatus are described in (1) U.S. Pat. No. 5,300,101, which issued on Apr. 5, 1994 in the names of Augustine et al., and is assigned to the Assignee of the present invention, and (2) U.S. patent application Ser. No. 08/386,989, which was filed on Feb. 6, 1995 in the name of Scott D. Augustine, and is assigned to the Assignee of the present invention, now U.S. Pat. No. 5,674,269.

An inflatable convective thermal care apparatus, such as described above, employs a medium source to provide a thermally-controlled inflating medium at a controlled rate, usually through an outlet duct such as a sealed delivery tube. Often, the medium source comprises an electrically driven motor coupled to a fluid conditioning element such as a heating or cooling element. In an exemplary embodiment, the thermal care apparatus may utilize heated air to treat a hypothermic patient; in this embodiment, the media source first collects and filters input air, then heats the air, and finally blows the air through the outlet duct to the thermal care apparatus.

The convective thermal care apparatus and associated medium source have benefitted numerous users, many of who have found them to be completely satisfactory for their needs. However, in certain situations, patients and medical personnel alike would benefit from having a medium source that operated with reduced noise. Some patients, for example, may be more sensitive to noise due to their medical condition. Additionally, the operating room must be kept quiet to avoid distracting the operating team, and to aid the doctors and nurses in hearing vital sign monitors. Furthermore, quiet surroundings are desirable in post-operative recovery rooms, to help patients gently emerge from anesthesia-induced sleep.

In view of the above considerations, some users might benefit by having a fluid source that operates with reduced noise in providing a regulated supply of thermally-controlled inflating medium.

SUMMARY OF THE INVENTION

One aspect of the present invention concerns an electrically operated medium source that employs active noise cancellation to reduce motor noise, while providing a source of thermally-controlled inflating medium to inflate a convective thermal care apparatus used to thermally treat hospital patients. In an illustrative application of the invention, the medium source may be used to provide warmed air to treat a potentially hypothermic patient before, during, or after a medical procedure such as surgery.

The medium source generally includes a housing, noise cancelling components, and temperature regulating components. In accordance with one application, the housing collects thermally-controlled inflating medium with a blower, which creates a medium stream that flows through the housing and exits through an outlet duct. The outlet duct may be connected to a thermal care apparatus.

The temperature regulating components of the invention include a conditioning unit, a temperature sensor, and a temperature controller. The conditioning unit warms or cools inflating medium collected by the blower. The temperature sensor measures the warmed or cooled medium's temperature and provides an electrical output signal representative of the measured temperature. The temperature controller, which is electrically connected to the medium conditioning unit and the temperature sensor, regulates the operation of the conditioning unit in response to the temperature sensor's measurements. Specifically, the controller adjusts the duty cycle of the conditioning unit to warm or cool the inflating medium to a specific user-selected desired temperature.

The noise cancelling components of the invention include an input microphone, a loudspeaker, an optional error microphone, and a noise cancellation controller that is connected to each of the other components. The input microphone detects sound proximate the housing and creates a representative electrical signal. The noise cancellation controller receives the input signal provided by the input microphone, and based on this signal, generates an electrical signal calculated to cancel the input signal when the two are added. This electrical signal is directed to the loudspeaker, which produces an audible noise-cancelling signal, 180° out of phase with the noise measured by the input microphone, to effectively cancel that noise. Any remaining noise is measured by the error microphone, and used as feedback by the noise cancellation controller to eliminate that remaining noise.

In a specific implementation, the invention may be used to treat hypothermic patients by directing a stream of temperature-regulated warmed air into a convective blanket or a convective bathing device, with reduced noise. A different aspect of the invention includes a method of supplying thermally-controlled inflating medium with an improved medium source to treat a patient, while actively reducing noise created by the medium source. Like the apparatus of the invention, this method may be specifically implemented to treat hypothermic patients with warmed air.

By providing a regulated stream of thermally controlled inflating medium while reducing noise, the present invention affords its users with a number of distinct advantages. For example, the invention is less likely to bother patients whose medical conditions cause heightened sensitivity to background noise. Additionally, the medium source of the invention helps keep the operating room quiet, so that medical personnel can tend to the patient's needs without distraction. Moreover, the inflating medium delivery system of the invention does not disturb patients during post-operative recovery.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

General Structure

Figure 1:
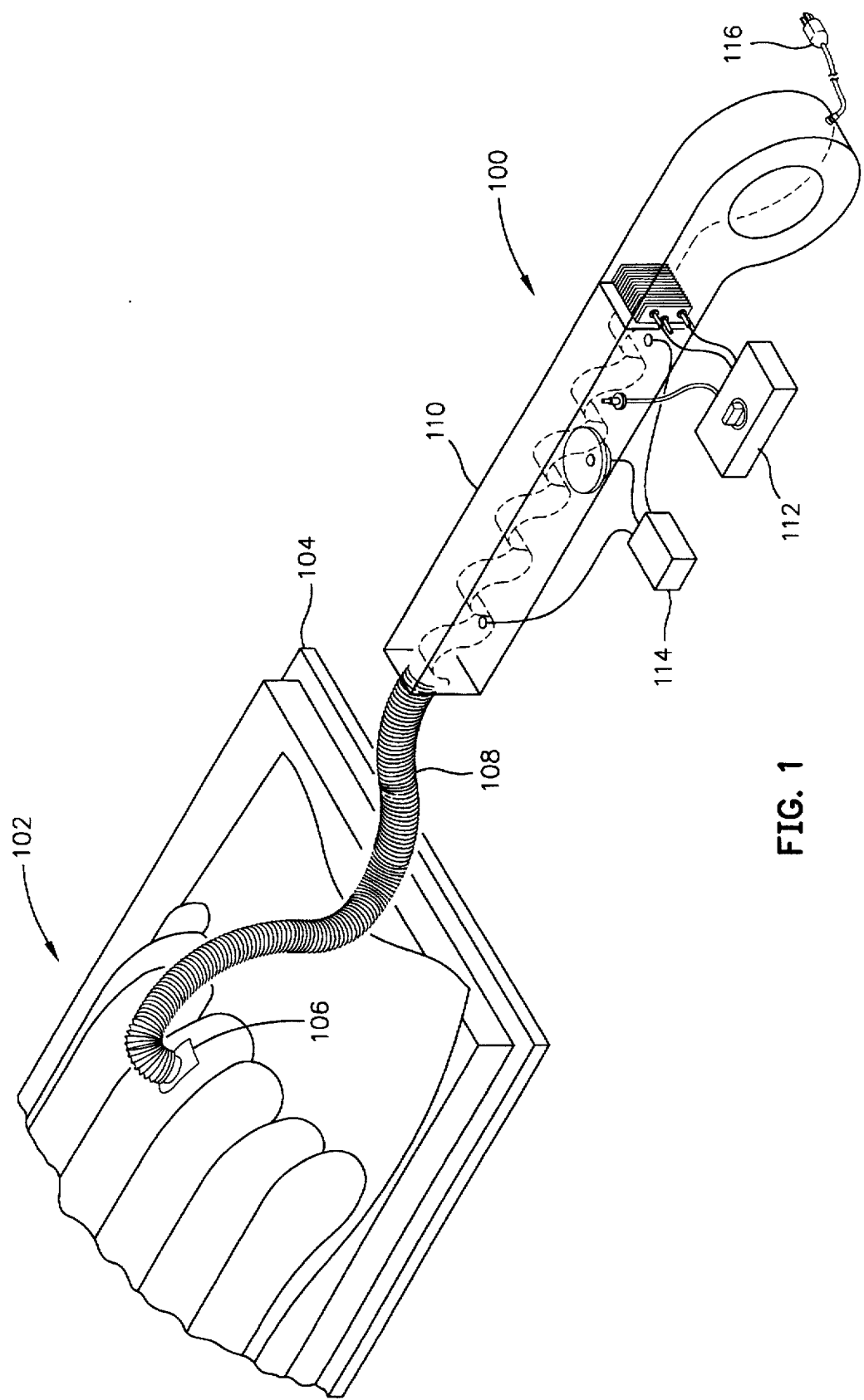
FIG. 1 is a perspective view of the inflating medium source 100 of the invention in an exemplary application.

Referring to FIG. 1, one aspect of the present invention comprises an electrically operated source 100 of an inflating medium that employs active noise cancellation to reduce noise, while providing a source of thermally-controlled medium to inflate a convective thermal care apparatus 102 used to treat a hospital patient (not shown). In an illustrative application of the invention, the source 100 may be used to provide warmed air to treat a potentially hypothermic patient before, during, or after a medical procedure such as surgery.

The source 100 is placed behind a hospital bed, or in another unobtrusive location, while the thermal care apparatus 102 is positioned over the patient. The patient may reside on a flat surface 104 such as a hospital bed. The thermal care apparatus includes an inlet 106 connected to the source 100 by a flexible outlet duct 108. The source 100 includes a housing 110, a noise cancellation controller 114, a temperature controller 112, and an electrical cord 116 to couple the source 100 to a source of electrical power (not shown). The source 100 also includes various noise cancelling components and temperature components, which are described below.

Figure 2:
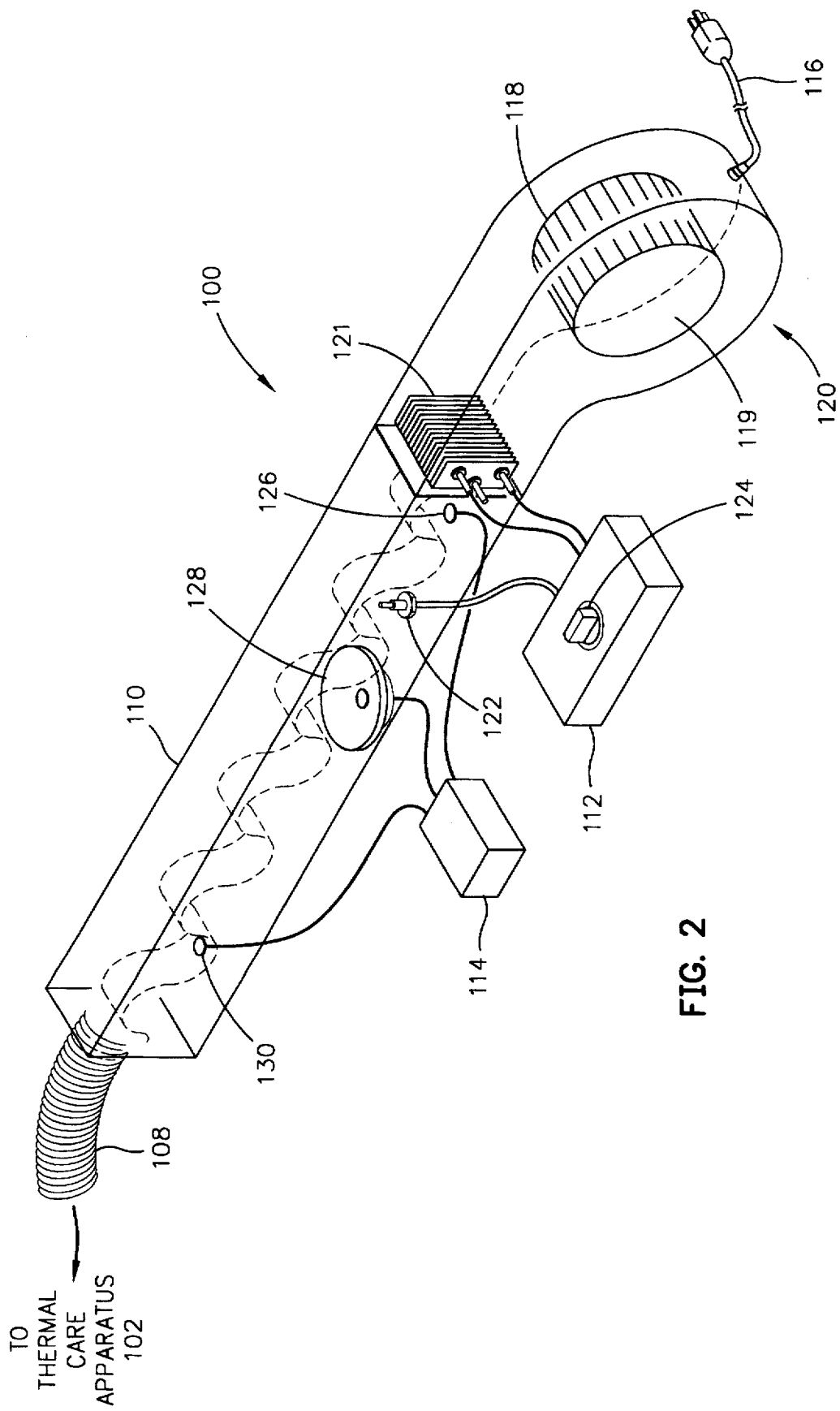
FIG. 2 is a more detailed perspective view of the inflating medium source 100 of the invention.

Referring to FIG. 2, the housing 110 may collect the thermally-controlled inflating medium with a blower 118, which creates a medium stream (not shown) that flows through the housing 110 and to the outlet duct 108. In this respect, the housing 110 is elongated to assist in generating a stream of inflating medium that will efficiently flow into the outlet duct 108. The outlet duct 108 preferably includes a fitting (not shown) to sealably couple the housing 110 to the duct 108. In the preferred embodiment, the blower 118 comprises an electrically-powered "squirrel cage" blower with a medium throughput of 35 cubic feet per minute. In an alternative embodiment, however, the blower 118 may comprise one or more fan blades to move the inflating medium through the housing 110. The medium may comprise a variety of different substances, but preferably comprises a non-toxic oxygen-based gas such as air. In the preferred embodiment, the blower 118 intakes the medium by drawing air through an inlet ring 119 defined in the housing.

The source 100 also includes a number of temperature regulating components, including a conditioning unit 121, a temperature sensor 122, and the temperature controller 112. The conditioning unit 121 warms or cools medium collected by the blower 118. In applications requiring the unit 121 to perform heating, the unit 121 preferably comprises a heating element rated between 600 and 800 watts, such as a finned copper pipe containing a potted heat dissipating resistor, or an array of resistive wires. Alternatively, in applications requiring the unit 121 to perform cooling, the unit 121 preferably comprises a thermoelectric cooling circuit or a refrigeration unit.

The temperature sensor 122 preferably comprises a thermocouple for sensing the temperature of medium within the housing 110, and providing an electrical output signal representative of the sensed temperature. Alternatively, the sensor 122 may be implemented in the form of a thermistor, thermoelectric junction, bimetallic strip, or another temperature sensing device. The temperature sensor 122 may be mounted, as an example, near the conditioning unit 121.

The temperature controller 112, which is electrically connected to the conditioning unit 121 and the temperature sensor 122, regulates the operation of the conditioning unit 121 in response to the temperature measurements of the sensor 122. Specifically, the controller 112 increases or decreases the duty cycle of the conditioning unit 121 as needed to warm or cool the inflating medium to a specific user-selected temperature. The user-selected temperature may be input to the controller 122, in a typical embodiment, by a mechanical switch 124 such as a dial, rheostat, lever, knob, or another suitable input device.

The source 100 of the invention additionally includes a number of noise cancelling components, as described more fully below. In accordance with the present invention, it has been discovered that most of the noise generated by a convective thermal care apparatus is attributable to the blower and the conditioning unit. The blower-induced noise is primarily generated by the rotating tips of the blower blades. Another source of noise is the turbulent rush of air flowing through the housing 110 and conditioning unit 121. Much of this noise occurs in the lower audible frequencies, generally below 500 Hz, and chiefly comprises repetitive tones. Although this noise is most prevalent near the housing and outlet duct 108, a significant amount of the noise is transmitted through the outlet duct 108 toward the patient. Many of these characteristics make the noise created by the fluid source especially susceptible to noise reduction using active noise cancellation technology.

Accordingly, the noise cancelling components of the invention include an input sensor such as a microphone 126, a sound source such as a loudspeaker 128, a noise cancellation controller 114, and an optional error microphone 130. The noise cancellation controller 114 is electrically connected to each of the other noise cancelling components. The input microphone 126 comprises a sensitive audio element for sensing sound and generating a representative first electrical signal. The input microphone 126 is preferably located near the conditioning unit 121 and the blower 118, since the majority of noise created by the source 100 is created by these parts.

The loudspeaker 128 comprises an audio element for producing a cancelling sound in response to a second electrical signal. As described in greater detail below, the loudspeaker 128 functions in response to the second signal to produce an audible noise-cancelling signal, 180° out of phase with the noise measured by the input microphone 126, to effectively cancel out that noise. For optimal noise-cancelling efficiency, the loudspeaker 128 is preferably positioned in the housing 100, since most of the noise emanates from the blower 118 and the conditioning unit 121. Alternatively, the loudspeaker 128 may be positioned in the outlet duct 108 to prevent noise from the housing 110 from reaching the thermal care apparatus 102.

The noise cancellation controller 114 receives the first electrical signal provided by the input microphone 126, and based on this signal, generates the second electrical signal such that the cancelling sound produced by the loudspeaker 128 cancels the sound comprising the noise created by the source 100 when the two sounds are added. This operation may be performed in accordance with a number of well known techniques, including adaptive finite impulse response filters and other suitable mathematical models. The noise cancellation controller 114 preferably comprises a DIGISONIX brand digital sound cancellation system, manufactured by Nelson Industries, Inc. of Middleton, Wis.

If further noise reduction is desired, the source 100 may include an error sensor such as a microphone 130 that, like the input microphone 126, comprises a sensitive audio element for detecting sound and generating a third electrical signal representing the sound detected by the mircophone 130. The microphone 130 is preferably located near the outlet duct 108, to most effectively measure the noise likely to be passed to the thermal care apparatus 102 through the outlet duct 108. The third electrical signal from the microphone 130 is directed to the noise cancellation controller 114, which uses this signal in generating the second electrical signal that is fed to the loudspeaker 128. Hence, the third signal from the microphone 130 is combined with the first signal by the controller 114 to condition the second signal so that the loudspeaker produces an audible noise-cancelling signal that optimally cancels most, if not all noise present at the input of the duct 108.

Operation

Referring now to all Figures, the fluid source 100 is used in the following manner. First, the patient is placed supine on a flat surface 104, such as a hospital bed. Then, the thermal care apparatus 102 comprising an Augustine-type thermal blanket is placed over the patient to create a thermal care zone (not shown) about the patient. After the outlet duct 108 is sealably coupled between the apparatus 102 and the source 100 of inflating medium, and the source 100 is activated.

In an illustrative embodiment, where the source 100 is used to warm air for treating a hypothermic patient, the blower 118 first collects air through the inlet ring 106 and directs the air toward the outlet duct 108, creating stream of air through the housing 110. En route to the outlet duct 108, the air inside the housing 110 is heated by the conditioning unit 121, according to the electrical inputs provided by the temperature controller 112. The temperature of the air warmed by the conditioning unit 121 is measured by the temperature sensor 122, which provides a representative electrical output signal to the controller 112.

In response to this output signal, the controller 112 identifies any error that exists between the measured temperature and the desired temperature of air, and adjusts the operation of the conditioning unit 121 in a manner calculated to achieve the desired air temperature.

Manifestly, the stream of inflating medium in the preferred embodiment comprises heated air.

While the air is being drawn into the housing 110 and heated, the noise cancelling components reduce the noise present in the housing 110. Specifically, the input microphone 126 measures the sound in the housing 110, and provides a representative output signal. The noise cancellation controller 114 receives this output signal and generates an electrical signal that, when made audible, is calculated to cancel the measured noise signal. The loudspeaker 128 receives this noise-cancelling signal and makes it audible. The error microphone 130 measures the amount of remaining noise proximate the outlet duct 108, and creates a representative electrical output signal. This output signal is fed to the controller 114, which uses this information as feedback to generate an improved noise cancelling signal, which is made audible by the loudspeaker 128.

When the source 100 is activated as described above, it provides a flow of heated air, which inflates the apparatus 102. Exhaust holes in the apparatus 102 then expel the heated air about the patient. Due to the reduction of noise by the noise cancelling components, the patient is not distracted by noise from the source 100. Or, if the patient is under surgery, the reduced noise of the source 100 assists the doctors and nurses similarly.

While there have been shown what is presently considered to be a preferred embodiment of the invention, it will be apparent to those skilled in the art that various changes and modifications can be made herein without departing from the scope of the invention as defined by the appended claims. For example, although specific references are made to the "inflating medium" and the use of "air," these are merely provided for an exemplary description, although the structure and function of the present invention are not so limited.

What is claimed is:

1. A source for supplying thermally-controlled inflating media to an inflatable convective thermal care apparatus used in thermally treating a patient, comprising:
   an outlet duct with first and second ends;
   a housing secured to the first end of the outlet duct;
   the second end of the outlet duct coupled to a fitting of an inflatable convective thermal care apparatus;
   a blower to collect an inflating medium and create a stream inflating medium moving through the housing and into the outlet duct, said stream of inflating medium having an original temperature;
   temperature regulating components, including:
      a conditioning element positioned in the stream of inflating medium to change the temperature of the medium to a conditioned temperature;
      a temperature sensor to measure the conditioned temperature of the medium and provide an output signal representative thereof;

a temperature controller, electrically connected to the temperature sensor, to control the conditioning element to produce a user-selected fluid temperature in the stream of inflating medium; and noise canceling components, including:

a sound sensor positioned in the housing to sense noise sound in the housing and provide a first signal representing the noise sound in the housing;

a sound source positioned in the housing to produce a noise-canceling sound signal responsive to a second signal; and a noise cancellation controller connected to the sound sensor to receive the first signal and connected to the sound source to provide the second signal such that the second signal causes the sound source to create a sound signal to substantially cancel the noise sound in the housing.

2. The source of claim 1, wherein the conditioning element comprises a heating apparatus.

3. The source of claim 1, wherein the conditioning element comprises a cooling apparatus.

4. The source of claim 1, wherein the inflating medium comprises air.

5. The source of claim 1, further including an error sound sensor to measure sound proximate the outlet duct and generate a third electrical signal proportionate thereto, wherein said error sound sensor is positioned a first distance from the outlet duct and the sound sensor is positioned a second distance from the outlet duct, and the first distance is less than the second distance.

6. The source of claim 5, wherein the noise cancellation controller receives the third electrical signal and generates the second signal in response to the first and third signals such that the noise cancelling sound signal cancels substantially all noise sound proximate the outlet duct.

7. The source of claim 1, wherein the sound sensor includes an input microphone positioned proximate the conditioning element.

8. The source of claim 7, wherein the sound source includes a loudspeaker positioned between the input microphone and the outlet duct.

9. A combination for treating a hospital patient that includes the source of claim 1, further including:

an inflatable thermal treatment apparatus; and an inlet ring on the inflatable thermal treatment apparatus for receiving the second end.

10. An airflow apparatus for treating a hospital patient comprising:

a flexible outlet duct having a first end and a second end;

a housing coupled to the first end for directing a flow of warmed air to the flexible outlet duct;

an inflatable thermal care apparatus having an inlet ring coupled to the second end of the flexible outlet duct;

a sound sensor in the housing for providing a first signal representing noise;

a sound source in the housing for producing a noise canceling sound signal in response to a second signal; and a noise cancellation controller connected to the sound sensor and to the sound source for producing the second signal in response to the first signal.

11. The apparatus of claim 10, further including an error sound sensor to measure sound proximate the outlet duct and generate a third electrical signal proportionate thereto, wherein said error sound sensor is positioned a first distance from the outlet duct and the sound sensor is positioned a second distance from the outlet duct, and the first distance is less than the second distance.

12. The apparatus of claim 11, wherein the noise cancellation controller receives the third electrical signal and generates the second signal in response to the first and third signals such that the noise canceling sound signal cancels substantially all noise sound proximate the outlet duct.

13. The apparatus of claim 10, wherein the sound sensor includes an input microphone positioned proximate the housing.

14. The apparatus of claim 13, wherein the sound source includes a loudspeaker positioned between the input microphone and the outlet duct.

15. The apparatus of claim 10, further including means in the housing for creating the flow of warmed air.

* * * * *